(12) United States Patent
Kamenoue et al.

(10) Patent No.: US 12,703,838 B2
(45) **Date of Patent: *Aug. 11, 2026**

(54) COMPOUND, PRECURSOR COMPOUND THEREOF, SURFACTANT COMPOSITION, AND DETERGENT COMPOSITION

(71) Applicant: KAO CORPORATION, Tokyo (JP)

(72) Inventors: Shogo Kamenoue, Wakayama (JP); Akiyoshi Kimura, Wakayama (JP); Ojiro Tamagawa, Wakayama (JP)

(73) Assignee: KAO CORPORATION, Tokyo (JP)

( * ) Notice: Subject to any disclaimer, the term of this patent is extended or adjusted under 35 U.S.C. 154(b) by 477 days.

This patent is subject to a terminal disclaimer.

(21) Appl. No.: 18/035,318

(22) PCT Filed: Nov. 30, 2021

(86) PCT No.: PCT/JP2021/043846

§ 371 (c)(1),
(2) Date: May 4, 2023

(87) PCT Pub. No.: WO2022/114218

PCT Pub. Date: Jun. 2, 2022

(65) Prior Publication Data

US 2023/0407205 A1 Dec. 21, 2023

(30) Foreign Application Priority Data

Nov. 30, 2020 (JP) ................................ 2020-198429

(51) Int. Cl.

| | |
|---|---|
| ***C11D 3/20*** | (2006.01) |
| ***C07C 41/03*** | (2006.01) |
| ***C07C 43/13*** | (2006.01) |
| ***C08G 65/26*** | (2006.01) |
| ***C11D 1/72*** | (2006.01) |
| ***C11D 1/722*** | (2006.01) |
| ***C11D 3/26*** | (2006.01) |
| ***C11D 7/26*** | (2006.01) |

(52) U.S. Cl.

CPC ................ *C11D 1/72* (2013.01); *C07C 41/03* (2013.01); *C07C 43/135* (2013.01); *C08G 65/2609* (2013.01); *C11D 1/722* (2013.01); *C11D 3/20* (2013.01); *C11D 3/2041* (2013.01); *C11D 3/2044* (2013.01); *C11D 7/261* (2013.01); *C11D 7/262* (2013.01); *C11D 2111/12* (2024.01)

(58) Field of Classification Search

CPC .. C11D 1/72; C11D 1/722; C11D 3/20; C11D 3/2041; C11D 3/2044; C11D 7/261; C11D 7/262

USPC ........................................ 510/421, 505, 506

See application file for complete search history.

(56) References Cited

U.S. PATENT DOCUMENTS

| | | | | |
|---|---|---|---|---|
| 6,017,875 | A | 1/2000 | Kadono et al. | |
| 6,093,856 | A | 7/2000 | Cripe et al. | |
| 6,323,172 | B1 * | 11/2001 | Trinh | C11D 3/2093 510/516 |
| 9,896,648 | B2 * | 2/2018 | Scheibel | C07C 43/11 |
| 2016/0340625 | A1 | 11/2016 | Scheibel et al. | |
| 2017/0253839 | A1 * | 9/2017 | Scheibel | C11D 17/003 |
| 2022/0144741 | A1 | 5/2022 | Kamenoue et al. | |

FOREIGN PATENT DOCUMENTS

| | | | | |
|---|---|---|---|---|
| EP | 0 850 907 A2 | 7/1998 | | |
| JP | 55-105632 A | 8/1980 | | |
| JP | 2566821 B2 * | 12/1996 | | C11D 1/825 |
| JP | 10-168014 A | 6/1998 | | |

(Continued)

OTHER PUBLICATIONS

English Language Machine Translation of JP1990206696. (Year: 1990).*

English Language Machine Translation of JPH1990206696A. (Year: 1990).*

English Language Machine Translation of JP2566821. (Year: 1996).*

International Search Report for PCT/JP2021/043846 (PCT/ISA/210) mailed on Feb. 1, 2022.

Stropoli et al., "Assessing Potential Oligomerization Reaction Mechanisms of Isoprene Epoxydiols on Secondary Organic Aerosol", Environmental Science & Technology, 2019, vol. 53, No. 1, pp. 176-184.

(Continued)

*Primary Examiner* — Gregory R Delcotto

(74) *Attorney, Agent, or Firm* — Birch, Stewart, Kolasch & Birch, LLP

(57) ABSTRACT

The invention provides a compound of chemical formula (1), a precursor compound for producing the compound, a surfactant composition and a detergent composition including the compound,

[Chemical Formula (1)]

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^1$ is $—O(-A^{11}O)_l—H$, $A^2$ is $—O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$, $A^{11}$, $A^{21}$, $A^{22}$, $A^{23}$, and $A^{24}$ are each independently an alkanediyl group having 2 or more and 8 or less carbon atoms, l, m, n, s, and t are an average value and are each independently 0 or more, and a total of l, m, and n, and a total of l, s, and t are each independently more than 0 and 200 or less.

20 Claims, No Drawings

(56) References Cited

FOREIGN PATENT DOCUMENTS

| | | | |
|---|---|---|---|
| JP | 11-349507 | A | 12/1999 |
| JP | 2001-2715 | A | 1/2001 |
| JP | 2005-225788 | A | 8/2005 |
| WO | WO 97/22651 | A1 | 6/1997 |
| WO | WO 2007/062112 | A2 | 5/2007 |
| WO | WO 2020/241771 | A1 | 12/2020 |

OTHER PUBLICATIONS

English translation of the International Preliminary Report on Patentability and Written Opinion of the International Searching Authority for International Application No. PCT/JP2021/043846, dated Jun. 15, 2023.

Extended European Search Report for European Application No. 21898189.2, dated May 6, 2024.

* cited by examiner

COMPOUND, PRECURSOR COMPOUND THEREOF, SURFACTANT COMPOSITION, AND DETERGENT COMPOSITION

TECHNICAL FIELD

The present invention relates to a compound and a precursor compound for producing the compound. The present invention also relates to a surfactant composition and a detergent composition that include the compound.

BACKGROUND ART

Nonionic surfactants are used in a wide range of fields such as laundry detergents, dishwashing detergents, residential detergents, body cleansers, iron and steel cleaning, and precision cleaning. The required performance of the nonionic surfactants is, for example, high detergency, compatibility with products, and easiness of handling.

Examples of the nonionic surfactants include an alkylphenol ethoxylate, a higher primary alcohol ethoxylate, a higher secondary alcohol ethoxylate, and a fatty acid ethoxylate. Among these examples, an alkylphenol ethoxylate, particularly nonylphenol ethoxylate which has poor biodegradability and therefore possibly adversely affects the environment is being restricted.

Patent Document 1 discloses a higher secondary alcohol alkoxylate adduct obtained by adding a (poly)alkylene glycol to a double bond of a long-chain olefin to give a higher secondary alcohol alkoxylate, and further adding an alkylene oxide to the higher secondary alcohol alkoxylate. The higher secondary alcohol alkoxylate adduct is described as having a low pour point, being easily handled, and having good penetrating ability, a good rinse-aid quality, and excellent detergency and emulsifying ability.

PRIOR ART DOCUMENTS

Patent Documents

Patent Document 1: JP-A-10-168014

SUMMARY OF THE INVENTION

Problems to be Solved by the Invention

The higher secondary alcohol alkoxylate adduct in Patent Document 1, however, has not been able to sufficiently satisfy the detergency and the rinse-aid quality.

The present invention has been made in view of the circumstances described above, and provides a compound that exhibits high detergency and a rapid foam-breaking quality, and a precursor compound for producing the compound. The present invention also provides a surfactant composition and a detergent composition that include the compound.

Means for Solving the Problems

As a result of an earnest study, the inventors of the present invention have found that the problems can be solved by a compound having a following specific structure.

The present invention relates to a compound represented by a chemical formula (1) below:

[Chemical Formula (1)]

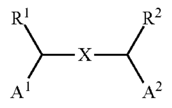

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^1$ is $—O(-A^{11}O)_l—H$, $A^2$ is $—O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$, $A^{11}$, $A^{21}$, $A^{22}$, $A^{23}$, and $A^{24}$ are each independently an alkanediyl group having 2 or more and 8 or less carbon atoms, l, m, n, s, and t are an average value and are each independently 0 or more, and a total of l, m, and n, and a total of l, s, and t are each independently more than 0 and 200 or less.

The present invention relates to a precursor compound for producing the compound represented by the chemical formula (1), the precursor compound being represented by a chemical formula (2) below:

[Chemical Formula (2)]

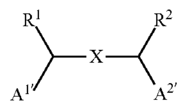

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is —OH, and $A^{2'}$ is $—O—CH_2—CH(OH)—CH_2OH$ or $—O—CH(—CH_2OH)_2$.

The present invention relates to use of the precursor compound represented by the chemical formula (2), for producing the compound represented by the chemical formula (1).

The present invention relates to a method for producing the compound represented by the chemical formula (1), including a process of adding an alkylene oxide having 2 or more and 8 or less carbon atoms to the precursor compound represented by the chemical formula (2).

Effect of the Invention

The compound (hereinafter, also referred to as an internal three hydrophilic groups-containing compound) represented by the chemical formula (1) of the present invention has a rapid foam-breaking quality because the compound includes a hydrophobic group and a hydrophilic group both having multiple chains, and has a structure in which molecules are very much less likely to be oriented. The internal three hydrophilic groups-containing compound according to the present invention includes a long-chain alkyl group and a plurality of hydrophilic groups consolidated in a compact manner, and therefore has high surface-active performance and exhibits high detergency. A detergent composition according to the present invention containing the internal three hydrophilic groups-containing compound is considered to be likely to form a D phase (bicontinuous structure), and therefore the detergent composition exhibits high detergency even with a low concentration of the internal three hydrophilic groups-containing compound therein, is less likely to cause gelation or thickening in a wide range of concentration, and has excellent handling properties.

MODE FOR CARRYING OUT THE INVENTION

Hereinafter, a detailed described is made of the present invention.

<Internal Three Hydrophilic Groups-Containing Compound>

The internal three hydrophilic groups-containing compound of the present invention is a compound represented by the chemical formula (1) below:

[Chemical Formula (1)]

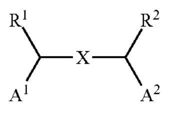

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^1$ is $—O(-A^{11}O)_l—H$, $A^2$ is $—O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$, $A^{11}$, $A^{21}$, $A^{22}$, $A^{23}$, and $A^{24}$ are each independently an alkanediyl group having 2 or more and 8 or less carbon atoms, l, m, n, s, and t are an average value and are each independently 0 or more, and a total of l, m, and n, and a total of l, s, and t are each independently more than 0 and 200 or less.

$R^1$ and $R^2$ are each an aliphatic hydrocarbon group, and are each preferably a linear or branched alkyl group, more preferably a linear alkyl group, further preferably a linear primary alkyl group, from the viewpoints of production efficiency and easiness of production. $R^1$ and $R^2$ each independently have 1 or more and 33 or less carbon atoms and may each have a carbon number distribution. $R^1$ and $R^2$ may be a same aliphatic hydrocarbon group or different aliphatic hydrocarbon groups.

In the chemical formula (1), X is a single bond or a hydrocarbon group having 1 or more and 5 or less carbon atoms, and is preferably a single bond or a hydrocarbon group having 1 or more and 3 or less carbon atoms, more preferably a single bond or a hydrocarbon group having 1 or more and 2 or less carbon atoms, further preferably a single bond or a hydrocarbon group having 1 carbon atom, still further preferably a single bond, from the viewpoints of production efficiency and easiness of production.

The total number of carbon atoms of $R^1$, $R^2$, and X is 2 or more and 39 or less, is preferably 10 or more, more preferably 12 or more, further preferably 14 or more from the viewpoint of improving detergency, and is preferably 20 or less, more preferably 18 or less, further preferably 16 or less from the viewpoint of improving water solubility.

The total number of carbon atoms of $R^1$, $R^2$, and X is preferably even from the viewpoint of easiness of obtaining a raw material.

The internal three hydrophilic groups-containing compound preferably includes two or more compounds that have a same total number of carbon atoms of $R^1$, $R^2$, and X, but are different in number of carbon atoms of each of $R^1$ and $R^2$, from the viewpoints of production efficiency and easiness of production.

The internal three hydrophilic groups-containing compound more preferably includes two or more compounds that have a single bond as X and a same total number of carbon atoms of $R^1$, $R^2$, and X, but are different in number of carbon atoms of each of $R^1$ and $R^2$, from the viewpoints of production efficiency and easiness of production.

When the internal three hydrophilic groups-containing compound includes two or more compounds that have a single bond as X, and are different in total number of carbon atoms of $R^1$ and $R^2$, the total content of a compound having a total number of carbon atoms of $R^1$ and $R^2$ of 14 and a compound having a total number of carbon atoms of $R^1$ and $R^2$ of 16 is, in the whole internal three hydrophilic groups-containing compound, preferably 75 mass % or more, more preferably 85 mass % or more, further preferably 95 mass % or more, still further preferably 100 mass %, from the viewpoint of improving detergency and foam-breaking speed.

When being a hydrocarbon group, X is preferably a linear or branched alkanediyl group, more preferably a linear alkanediyl group, further preferably a linear $\alpha,\omega$-alkanediyl group, from the viewpoints of production efficiency and easiness of production.

When the internal three hydrophilic groups-containing compound includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole internal three hydrophilic groups-containing compound, preferably 10 mass % or more, more preferably 20 mass % or more, further preferably 30 mass % or more, and preferably 90 mass % or less, more preferably 80 mass % or less, further preferably 70 mass % or less, from the viewpoint of improving detergency and foam-breaking speed.

In the chemical formula (1), Al is $—O(-A^{11}O)_l—H$, and $A^2$ is $—O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$.

When a compound in which $A^2$ is $—O—CH_2—CH(—O(-A^{21}O)_m—H)(—CH_2—O(-A^{22}O)_n—H)$ is defined as T1, and a compound in which $A^2$ is $—O—CH(—CH_2—O(-A^{23}O)_s—H)(—CH_2—O(-A^{24}O)_t—H)$ is defined as T2, the molar proportion [T1/(T1+T2)] of T1 to the total of T1 and T2 is preferably 0.5 or more, more preferably 0.6 or more, further preferably 0.7 or more, and preferably 0.9 or less, more preferably 0.85 or less, further preferably 0.8 or less, from the viewpoint of easiness of production.

$A^{11}O$, $A^{21}O$, $A^{22}O$, $A^{23}O$, and $A^{24}O$ are each an alkyleneoxy group, and $A^{11}$, $A^{21}$, $A^{22}$, $A^{23}$, and $A^{24}$ are each independently an alkanediyl group having 2 or more and 8 or less carbon atoms. The alkanediyl group is preferably a 1,2-alkanediyl group from the viewpoint of easiness of production, is more preferably one or more selected from an ethanediyl group or a 1,2-propanediyl group from the viewpoint of improving detergency, defoaming properties, and water solubility, and is further preferably an ethanediyl group from the viewpoint of detergency. The number of carbon atoms of the alkanediyl group is preferably 2 or more and 6 or less, more preferably 2 or more and 5 or less, further preferably 2 or more and 4 or less, still further preferably 2 or 3 from the viewpoint of improving detergency, defoaming properties, and water solubility, is still further preferably 2 from the viewpoint of detergency, and is still further preferably 3 from the viewpoint of defoaming properties. That is, the number of carbon atoms of the alkanediyl group is preferably 6 or less, more preferably 5 or less, further preferably 4 or less, still further preferably 2 or 3 from the same viewpoint, is still further preferably 2 from the viewpoint of detergency, and is still further preferably 3 from the viewpoint of defoaming properties. Examples of the alkyleneoxy group include an ethyleneoxy group, a branched alkyleneoxy group having 3 or more and 8 or less carbon atoms, and a linear alkyleneoxy group having 3 or more and 8 or less carbon atoms. The alkyleneoxy group is preferably an ethyleneoxy group or a branched alkyleneoxy group having 3 or more and 8 or less carbon atoms. l pieces of $A^{11}O$, m pieces of $A^{21}O$, n pieces of $A^{22}O$, s pieces of $A^{23}O$, and t pieces of $A^{24}O$ may each independently include one type of the alkyleneoxy group or two or more types of the alkyleneoxy groups. Even when the internal three hydrophilic groups-containing compound includes two or more compounds that are different in number of pieces of $A^{11}O$, $A^{21}O$, $A^{22}O$, $A^{23}O$, or $A^{24}O$, l, m, n, s, or t in the chemical formula (1) represents the average value of the total number of alkyleneoxy groups.

When l pieces of $A^{11}O$, m pieces of $A^{21}O$, n pieces of $A^{22}O$, s pieces of $A^{23}O$, or t pieces of $A^{24}O$ include two or more types of the alkyleneoxy groups, the alkyleneoxy groups are preferably an ethyleneoxy group and one or more types of branched alkyleneoxy groups having 3 or more and 8 or less carbon atoms, more preferably an ethyleneoxy group and a branched propyleneoxy group. When l pieces of $A^{11}O$, m pieces of A210, n pieces of $A^{22}O$, s pieces of $A^{23}O$, or t pieces of $A^{24}O$ include an ethyleneoxy group and one or more types of branched alkyleneoxy groups having 3 or more and 8 or less carbon atoms (or a branched propyleneoxy group), the molar ratio (ethyleneoxy group/branched alkyleneoxy group having 3 or more and 8 or less carbon atoms (or branched propyleneoxy group) of the ethyleneoxy group to the branched alkyleneoxy group having 3 or more and 8 or less carbon atoms (or the branched propyleneoxy group) is preferably 2/8 or more, more preferably 3/7 or more from the viewpoint of improving detergency and water solubility, and is preferably 8/2 or less, more preferably 7/3 or less from the viewpoints of foam-breaking speed and prevention of gelation.

When l pieces of $A^{11}O$, m pieces of $A^{21}O$, n pieces of $A^{22}O$, s pieces of $A^{23}O$, or t pieces of $A^{24}O$ include two or more types of the alkyleneoxy groups, the repeating structure of the alkyleneoxy groups may include a random structure, a block structure, or a combination of a random structure and a block structure. The repeating structure, however, includes preferably a block structure, more preferably an EO block-PO block structure, a PO block-EO block structure, an EO block-PO block-EO block structure, or a PO block-EO block-PO block structure, further preferably an EO block-PO block-EO block structure, from the viewpoint of prevention of gelation.

In the chemical formula (1), l, m, n, s, and t are an average value and are each independently 0 or more, and the total of l, m, and n, and the total of l, s, and t are each independently more than 0 and 200 or less. The total of l, m, and n, and the total of l, s, and t are preferably 3 or more, more preferably 5 or more, further preferably 7 or more, still further preferably 9 or more from the viewpoint of improving detergency, foam-breaking speed, and water solubility, and is preferably 40 or less, more preferably 30 or less, further preferably 25 or less, still further preferably 20 or less from the viewpoints of improving detergency and foam-breaking speed and preventing gelation.

The method for producing the internal three hydrophilic groups-containing compound is not particularly limited, and the internal three hydrophilic groups-containing compound can be produced, for example, by oxidizing a double bond of an internal olefin with a peroxide such as hydrogen peroxide and peracetic acid to synthesize an internal epoxide, adding glycerin to the obtained internal epoxide to synthesize an internal alkyl glyceryl ether (hereinafter, also described as an AGE), and adding to the obtained internal alkyl glyceryl ether an alkylene oxide having 2 or more and 8 or less carbon atoms. When the internal olefin is a mixed product of two or more internal olefins that have a same total number of carbon atoms but a double bond at different positions therebetween, the internal three hydrophilic groups-containing compound obtained by the above-described production method is a mixed product of two or more compounds that have a same total number of carbon atoms of $R^1$, $R^2$, and X, but are different in number of carbon atoms of each of $R^1$ and $R^2$. Further, the internal three hydrophilic groups-containing compound obtained by the above-described production method is normally a mixed product of a compound in which $A^1$ is $—O(-A^{11}O)_l—H$, and $A^2$ is $—O—CH_2—CH(—O(-A^{21}O)_m—H)$ $(—CH_2—O(-A^{22}O)_n—H)$ in the chemical formula (1), and a compound in which $A^1$ is $—O(-A^{11}O)_l—H$, and $A^2$ is $—O—CH(—CH_2—O(-A^{23}O)_s—H)(—CH_2—O(-A^{24}O)_t—H)$, in the chemical formula (1).

The internal olefin used for the production of the internal three hydrophilic groups-containing compound may contain a terminal olefin. In such a case, the content of the terminal olefin included in the olefin is, for example, 0.1 mass % or more, 0.2 mass % or more, and 5 mass % or less, 3 mass % or less, 2 mass % or less, 1 mass % or less, 0.5 mass % or less.

<Precursor Compound>

The precursor compound of the present invention is a precursor compound for producing the compound represented by the chemical formula (1), the precursor compound being represented by a chemical formula (2) below:

[Chemical Formula (2)]

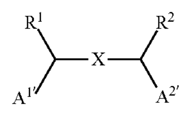

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is —OH, and $A^{2'}$ is $—O—CH_2—CH(OH)—CH_2OH$ or $—O—CH(—CH_2OH)_2$.

The aspects and suitable aspect of $R^1$ and $R^2$, and X in the chemical formula (2) are the same as the aspects and suitable aspects of $R^1$ and $R^2$, and X in the chemical formula (1).

The precursor compound preferably includes two or more compounds that have a same total number of carbon atoms of $R^1$, $R^2$, and X, but are different in number of carbon atoms of each of $R^1$ and $R^2$, from the viewpoints of production efficiency and easiness of production.

The precursor compound more preferably includes two or more compounds that have a single bond as X and a same total number of carbon atoms of $R^1$ and $R^2$, but are different in number of carbon atoms of each of $R^1$ and $R^2$, from the viewpoints of production efficiency and easiness of production.

When the precursor compound includes two or more compounds that have a single bond as X, and are different in total number of carbon atoms of $R^1$ and $R^2$, the total content of a compound having a total number of carbon atoms of $R^1$ and $R^2$ of 14 and a compound having a total number of carbon atoms of $R^1$ and $R^2$ of 16 is, in the whole precursor compound, preferably 75 mass % or more, more preferably 85 mass % or more, further preferably 95 mass % or more, still further preferably 100 mass %.

When the precursor compound includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole precursor compound, preferably 10 mass % or more, more preferably 20 mass % or more, further preferably 30 mass % or more, and preferably 90 mass % or less, more preferably 80 mass % or less, further preferably 70 mass % or less.

The method for producing the precursor compound is not particularly limited, and the precursor compound can be produced, for example, by oxidizing a double bond of an internal olefin with a peroxide such as hydrogen peroxide and peracetic acid to synthesize an internal epoxide, and adding glycerin to the obtained internal epoxide. When the internal olefin is a mixed product of two or more internal olefins that have a same total number of carbon atoms but a double bond at different positions therebetween, the precursor compound obtained by the above-described production method is a mixed product of two or more compounds that have a same total number of carbon atoms of $R^1$, $R^2$, and X, but are different in number of carbon atoms of each of $R^1$ and $R^2$. The precursor compound obtained by the above-described production method is normally a mixed product of a compound (P1) in which $A^{1'}$ is —OH, and $A^{2'}$ is —O—$CH_2$—CH(OH)—$CH_2OH$ in the chemical formula (2), and a compound (P2) in which $A^{1'}$ is —OH, and $A^{2'}$ is —O—CH(—$CH_2OH)_2$ in the chemical formula (2).

When the precursor compound is a mixed product of the compound (P1) and the compound (P2), the molar proportion [P1/(P1+P2)] of P1 to the total of P1 and P2 is preferably 0.5 or more, more preferably 0.6 or more, further preferably 0.7 or more, and preferably 0.9 or less, more preferably 0.85 or less, further preferably 0.8 or less, from the viewpoint of easiness of production.

The internal olefin used for the production of the precursor compound may contain a terminal olefin. In such a case, the content of the terminal olefin included in the olefin is, for example, 0.1 mass % or more, 0.2 mass % or more, and 5 mass % or less, 3 mass % or less, 2 mass % or less, 1 mass % or less, 0.5 mass % or less.

<Surfactant Composition>

A surfactant composition according to the present invention contains at least the internal three hydrophilic groups-containing compound.

The content of the internal three hydrophilic groups-containing compound in the surfactant composition is not particularly limited, but is preferably 50 mass % or more, more preferably 60 mass % or more, further preferably 70 mass % or more, still further preferably 80 mass % or more from the viewpoint of reducing transportation and storage costs, and is preferably 99 mass % or less, more preferably 95 mass % or less, further preferably 90 mass % or less from the viewpoint of prevention of gelation.

The surfactant composition according to the present invention preferably contains water from the viewpoint of easiness of handling. The water is not particularly limited, but is preferably purified water such as ion-exchanged water, distilled water, and reverse osmosis water.

The water can be used in the amount corresponding to the balance other than the internal three hydrophilic groups-containing compound and the other components. The content of the water in the composition can be set to 1 mass % or more, 5 mass % or more, 10 mass % or more, and can be set to 50 mass % or less, 40 mass % or less, 30 mass % or less, 20 mass % or less.

The surfactant composition according to the present invention can contain a surfactant or a solvent described below from the viewpoint of storage stability.

The addition of the solvent described below to the surfactant composition according to the present invention is not limited. From the viewpoints of sustainability, environmental burden, safety, and the like, however, the content of the solvent in the surfactant composition is preferably 10 mass % or less, more preferably 4 mass % or less, further preferably 1 mass % or less, still further preferably 0.1 mass % or less, still further preferably 0 mass %. That is, the surfactant composition preferably contains no solvent.

The surfactant composition may be an emulsifier composition, a wetting agent composition, or a penetrant composition. That is, the surfactant composition according to the present invention may be an emulsifier composition, a wetting agent composition, or a penetrant composition containing one or more compounds represented by the chemical formula (1).

<Detergent Composition>

A detergent composition according to the present invention contains at least the internal three hydrophilic groups-containing compound.

The content of the internal three hydrophilic groups-containing compound in the detergent composition is not particularly limited, but is preferably 0.1 mass % or more, more preferably 1 mass % or more, further preferably 10 mass % or more, still further preferably 30 mass % or more, still further preferably 40 mass % or more from the viewpoint of improving detergency and foam-breaking speed, and is preferably 99 mass % or less, more preferably 90 mass % or less, further preferably 80 mass % or less from the viewpoint of low-concentration detergency and prevention of gelation.

The detergent composition according to the present invention can contain any component used for detergents, such as a surfactant different from the internal three hydrophilic groups-containing compound, water, a solvent, fragrance, a dye, a defoamer, a preservative, a moisturizing agent, an antibacterial agent, an antidandruff agent, a pearlizing agent, a vitamin compound, a thickener, a pH adjuster, a bleacher, a chelating agent, a water-soluble salt, and an oil solution, as long as the component does not inhibit the effects of the present invention.

As the surfactant different from the internal three hydrophilic groups-containing compound, known surfactants can be used without any limitation. Examples of the surfactant include an anionic surfactant, a nonionic surfactant, an amphoteric surfactant, and a cationic surfactant.

The water is not particularly limited, but is preferably purified water such as ion-exchanged water, distilled water, and reverse osmosis water.

The water can be used in the amount corresponding to the balance other than the internal three hydrophilic groups-containing compound and the other components. The content of the water in the composition can be set to 1 mass % or more, 10 mass % or more, 20 mass % or more, 30 mass % or more, 40 mass % or more, 50 mass % or more, and can be set to 99.5 mass % or less, 90 mass % or less, 70 mass % or less, 60 mass % or less, 50 mass % or less, 40 mass % or less, 30 mass % or less, 20 mass % or less, 10 mass % or less, 5 mass % or less, 0 mass %.

The detergent composition according to the present invention can contain a solvent in order to, for example, increase low-temperature stability and washing performance.

The addition of the solvent described above to the detergent composition according to the present invention is not limited. From the viewpoints of sustainability, environmental burden, safety, and the like, however, the content of the solvent in the detergent composition is preferably 10 mass % or less, more preferably 4 mass % or less, further preferably 1 mass % or less, still further preferably 0.1 mass % or less, still further preferably 0 mass %. That is, the detergent composition preferably contains no solvent.

The detergent composition according to the present invention can be prepared, for example, by mixing the internal three hydrophilic groups-containing compound and a component other than the compound.

When the detergent composition containing another component is prepared, the preparation order is not particularly limited, and the detergent composition may be prepared by preparing a detergent composition containing the internal three hydrophilic groups-containing compound and then blending the other component in the detergent composition.

From the viewpoint of obtaining the detergent composition having the components uniformly dissolved therein, the detergent composition is preferably left to stand still at a prescribed temperature for a prescribed time after mixing. The temperature at which the detergent composition is left to stand still is preferably 10° C. or more, more preferably 15° C. or more, further preferably 20° C. or more, still further preferably 25° C. or more from the viewpoint of obtaining the detergent composition having the components uniformly dissolved therein, and is preferably 80° C. or less, more preferably 70° C. or less, further preferably 60° C. or less, still further preferably 50° C. or less, still further preferably 40° C. or less, still further preferably 30° C. or less from the viewpoint of economic efficiency. The time during which the detergent composition is left to stand still depends on the temperature, but is preferably 1 hour or more, more preferably 5 hours or more, further preferably 12 hours or more, still further preferably 18 hours or more, still further preferably 24 hours or more, still further preferably 2 days or more, still further preferably 3 days or more from the viewpoint of sufficiently uniformly dissolving the components, and is preferably 1 month or less, more preferably 20 days or less, further preferably 10 days or less from the viewpoint of economic efficiency.

The surfactant composition or the detergent composition according to the present invention is used as a detergent such as a laundry liquid detergent, a dishwashing detergent, shampoo, a body cleanser, a detergent for precision components, and a detergent for hard surfaces. The surfactant composition or the detergent composition according to the present invention can be added and dissolved in water and thereby applied to various washing uses described above.

The present invention and preferred embodiments of the present invention are described below.

<1>

A compound represented by a chemical formula (1) below:

[Chemical Formula (1)]

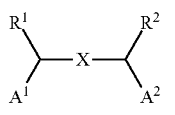

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^1$ is $—O(-A^{11}O)_l—H$, $A^2$ is $—O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$, $A^{11}$, $A^{21}$, $A^{22}$, $A^{23}$, and $A^{24}$ are each independently an alkanediyl group having 2 or more and 8 or less carbon atoms, l, m, n, s, and t are an average value and are each independently 0 or more, and a total of l, m, and n, and a total of l, s, and t are each independently more than 0 and 200 or less.

<2>

The compound according to <1>, wherein $R^1$ and $R^2$ are each preferably a linear or branched alkyl group, more preferably a linear alkyl group, further preferably a linear primary alkyl group.

<3>

The compound according to <1> or <2>, wherein $R^1$ and $R^2$ each independently have 1 or more and 33 or less carbon atoms.

<4>

The compound according to any one of <1> to <3>, wherein $R^1$ and $R^2$ are a same aliphatic hydrocarbon group or different aliphatic hydrocarbon groups.

<5>

The compound according to any one of <1> to <4>, wherein X is preferably a single bond or a hydrocarbon group having 1 or more and 3 or less carbon atoms, more preferably a single bond or a hydrocarbon group having 1 or more and 2 or less carbon atoms, further preferably a single bond or a hydrocarbon group having 1 carbon atom, still further preferably a single bond.

<6>

The compound according to any one of <1> to <4>, wherein X is a single bond.

<7>

The compound according to any one of <1> to <4>, wherein X is a hydrocarbon group having 1 or more and 5 or less carbon atoms.

<8>

The compound according to <7>, wherein the hydrocarbon group is preferably a linear or branched alkanediyl group, more preferably a linear alkanediyl group, further preferably a linear α,ω-alkanediyl group.

<9>

The compound according to any one of <1> to <8>, wherein the total number of carbon atoms of $R^1$, $R^2$, and X is preferably 10 or more, more preferably 12 or more, further preferably 14 or more, and is preferably 20 or less, more preferably 18 or less, further preferably 16 or less.

<10>

The compound according to any one of <1> to <8>, wherein the total number of carbon atoms of $R^1$, $R^2$, and X is 10 or more and 20 or less.

<11>

The compound according to any one of <1> to <8>, wherein the total number of carbon atoms of $R^1$, $R^2$, and X is 12 or more and 18 or less.

<12>

The compound according to any one of <1> to <8>, wherein the total number of carbon atoms of $R^1$, $R^2$, and X is 14 or more and 16 or less.

<13>

The compound according to any one of <1> to <12>, wherein the total number of carbon atoms of $R^1$, $R^2$, and X is even.

<14>

The compound according to any one of <1> to <13>, wherein the compound represented by the chemical formula (1) includes two or more compounds that have a same total number of carbon atoms of $R^1$, $R^2$, and X, but are different in number of carbon atoms of each of $R^1$ and $R^2$.

<15>

The compound according to any one of <1> to <13>, wherein the compound represented by the chemical formula (1) includes two or more compounds that have a single bond or a hydrocarbon group having 1 or more and 5 or less carbon atoms as X and a same total number of carbon atoms of $R^1$, $R^2$, and X, but are different in number of carbon atoms of each of $R^1$ and $R^2$.

<16>

The compound according to any one of <1> to <13>, wherein the compound represented by the chemical formula (1) includes two or more compounds that have a single bond or a hydrocarbon group having 1 or more and 3 or less carbon atoms as X and a same total number of carbon atoms of $R^1$, $R^2$, and X, but are different in number of carbon atoms of each of $R^1$ and $R^2$.

<17>

The compound according to any one of <1> to <13>, wherein the compound represented by the chemical formula (1) includes two or more compounds that have a single bond or a hydrocarbon group having 1 or more and 2 or less carbon atoms as X and a same total number of carbon atoms of $R^1$, $R^2$, and X, but are different in number of carbon atoms of each of $R^1$ and $R^2$.

<18>

The compound according to any one of <1> to <13>, wherein the compound represented by the chemical formula (1) includes two or more compounds that have a single bond or a hydrocarbon group having 1 carbon atom as X and a same total number of carbon atoms of $R^1$, $R^2$, and X, but are different in number of carbon atoms of each of $R^1$ and $R^2$.

<19>

The compound according to any one of <1> to <13>, wherein the compound represented by the chemical formula (1) includes two or more compounds that have a single bond as X and a same total number of carbon atoms of $R^1$, $R^2$, and X, but are different in number of carbon atoms of each of $R^1$ and $R^2$.

<20>

The compound according to any one of <1> to <13>, wherein when the compound represented by the chemical formula (1) includes two or more compounds that have a single bond as X, and are different in total number of carbon atoms of $R^1$ and $R^2$, the total content of a compound having a total number of carbon atoms of $R^1$ and $R^2$ of 14 and a compound having a total number of carbon atoms of $R^1$ and $R^2$ of 16 is preferably 75 mass % or more, more preferably 85 mass % or more, further preferably 95 mass % or more, still further preferably 100 mass %.

<21>

The compound according to any one of <1> to <13>, wherein when the compound represented by the chemical formula (1) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (1), preferably 10 mass % or more, more preferably 20 mass % or more, further preferably 30 mass % or more, and preferably 90 mass % or less, more preferably 80 mass % or less, further preferably 70 mass % or less.

<22>

The compound according to any one of <1> to <13>, wherein when the compound represented by the chemical formula (1) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (1), 10 mass % or more and 90 mass % or less.

<23>

The compound according to any one of <1> to <13>, wherein when the compound represented by the chemical formula (1) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (1), 20 mass % or more and 80 mass % or less.

<24>

The compound according to any one of <1> to <13>, wherein when the compound represented by the chemical formula (1) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (1), 30 mass % or more and 70 mass % or less.

<25>

The compound according to any one of <1> to <24>, wherein when a compound in which $A^2$ is $—O—CH_2—CH(—O(-A^{21}O)_m—H)(—CH_2—O(-A^{22}O)_n—H)$ is defined as T1, and a compound in which $A^2$ is $—O—CH(—CH_2—O(-A^{23}O)_s—H)(—CH_2—O(-A^{24}O)_t—H)$ is defined as T2, the molar proportion [T1/(T1+T2)] of T1 to the total of T1 and T2 is preferably 0.5 or more, more preferably 0.6 or more, further preferably 0.7 or more, and preferably 0.9 or less, more preferably 0.85 or less, further preferably 0.8 or less.

<26>

The compound according to any one of <1> to <24>, wherein when a compound in which $A^2$ is $—O—CH_2—CH(—O(-A^{21}O)_m—H)(—CH_2—O(-A^{22}O)_n—H)$ is defined as T1, and a compound in which $A^2$ is $—O—CH(—CH_2—O(-A^{23}O)_s—H)(—CH_2—O(-A^{24}O)_t—H)$ is defined as T2, the molar proportion [T1/(T1+T2)] of T1 to the total of T1 and T2 is 0.5 or more and 0.9 or less.

<27>

The compound according to any one of <1> to <24>, wherein when a compound in which $A^2$ is $—O—CH_2—CH(—O(-A^{21}O)_m—H)(—CH_2—O(-A^{22}O)_n—H)$ is defined as T1, and a compound in which $A^2$ is $—O—CH(—CH_2—O(-A^{23}O)_s—H)(—CH_2—O(-A^{24}O)_t—H)$ is defined as T2, the molar proportion [T1/(T1+T2)] of T1 to the total of T1 and T2 is 0.6 or more and 0.85 or less.

<28>

The compound according to any one of <1> to <24>, wherein when a compound in which $A^2$ is $—O—CH_2—CH(—O(-A^{21}O)_m—H)(—CH_2—O(-A^{22}O)_n—H)$ is defined as T1, and a compound in which $A^2$ is $—O—CH(—CH_2—O(-A^{23}O)_s—H)(—CH_2—O(-A^{24}O)_t—H)$ is defined as T2, the molar proportion [T1/(T1+T2)] of T1 to the total of T1 and T2 is 0.7 or more and 0.8 or less.

<29>

The compound according to any one of <1> to <28>, wherein the alkanediyl group is preferably a 1,2-alkanediyl group, more preferably one or more selected from an ethanediyl group or a 1,2-propanediyl group, and further preferably an ethanediyl group.

<30>

The compound according to any one of <1> to <28>, wherein the number of carbon atoms of the alkanediyl group is preferably 2 or more and 6 or less, more preferably 2 or more and 5 or less, further preferably 2 or more and 4 or less, still further preferably 2 or 3.

<31>

The compound according to any one of <1> to <28>, wherein the number of carbon atoms of the alkanediyl group is preferably 6 or less, more preferably 5 or less, further preferably 4 or less, still further preferably 2 or 3.

<32>

The compound according to any one of <1> to <28>, wherein $A^{11}O$, $A^{21}O$, $A^{22}O$, $A^{23}O$, and $A^{24}O$ are each an alkyleneoxy group, and the alkyleneoxy group is an ethyleneoxy group, or a branched alkyleneoxy group having 3 or more and 8 or less carbon atoms.

<33>

The compound according to any one of <1> to <32>, wherein when l pieces of $A^{11}O$, m pieces of $A^{21}O$, n pieces of $A^{22}O$, s pieces of $A^{23}O$, or t pieces of $A^{24}O$ include two or more types of the alkyleneoxy groups, the alkyleneoxy groups are preferably an ethyleneoxy group and one or more types of branched alkyleneoxy groups having 3 or more and 8 or less carbon atoms, more preferably an ethyleneoxy group and a branched propyleneoxy group.

<34>

The compound according to any one of <1> to <32>, wherein when l pieces of $A^{11}O$, m pieces of $A^{21}O$, n pieces of $A^{22}O$, s pieces of $A^{23}O$, or t pieces of $A^{24}O$ include an ethyleneoxy group and one or more types of branched alkyleneoxy groups having 3 or more and 8 or less carbon atoms (or a branched propyleneoxy group), the molar ratio (ethyleneoxy group/branched alkyleneoxy group having 3 or more and 8 or less carbon atoms (or branched propyleneoxy group) of the ethyleneoxy group to the branched alkyleneoxy group having 3 or more and 8 or less carbon atoms (or the branched propyleneoxy group) is preferably $2/8$ or more, more preferably $3/7$ or more, and is preferably $8/2$ or less, more preferably $7/3$ or less.

<35>

The compound according to any one of <1> to <32>, wherein when l pieces of $A^{11}O$, m pieces of $A^{21}O$, n pieces of $A^{22}O$, s pieces of $A^{23}O$, or t pieces of $A^{24}O$ include an ethyleneoxy group and one or more types of branched alkyleneoxy groups having 3 or more and 8 or less carbon atoms (or a branched propyleneoxy group), the molar ratio (ethyleneoxy group/branched alkyleneoxy group having 3 or more and 8 or less carbon atoms (or branched propyleneoxy group) of the ethyleneoxy group to the branched alkyleneoxy group having 3 or more and 8 or less carbon atoms (or the branched propyleneoxy group) is preferably $2/8$ or more and $8/2$ or less.

<36>

The compound according to any one of <1> to <32>, wherein when l pieces of $A^{11}O$, m pieces of $A^{21}O$, n pieces of $A^{22}O$, s pieces of $A^{23}O$, or t pieces of $A^{24}O$ include an ethyleneoxy group and one or more types of branched alkyleneoxy groups having 3 or more and 8 or less carbon atoms (or a branched propyleneoxy group), the molar ratio (ethyleneoxy group/branched alkyleneoxy group having 3 or more and 8 or less carbon atoms (or branched propyleneoxy group) of the ethyleneoxy group to the branched alkyleneoxy group having 3 or more and 8 or less carbon atoms (or the branched propyleneoxy group) is preferably $3/7$ or more and $7/3$ or less.

<37>

The compound according to any one of <1> to <36>, wherein when l pieces of $A^{11}O$, m pieces of $A^{21}O$, n pieces of $A^{22}O$, s pieces of $A^{23}O$, or t pieces of $A^{24}O$ include two or more types of the alkyleneoxy groups, the repeating structure of the alkyleneoxy groups include preferably a block structure, more preferably an EO block-PO block structure, a PO block-EO block structure, an EO block-PO block-EO block structure, or a PO block-EO block-PO block structure, further preferably an EO block-PO block-EO block structure.

<38>

The compound according to any one of <1> to <37>, wherein the total of l, m, and n, and the total of l, s, and t are each independently preferably 3 or more, more preferably 5 or more, further preferably 7 or more, still further preferably 9 or more, and is preferably 40 or less, more preferably 30 or less, further preferably 25 or less, still further preferably 20 or less.

<39>

The compound according to any one of <1> to <37>, wherein the total of l, m, and n, and the total of l, s, and t are each independently preferably 3 or more and 40 or less.

<40>

The compound according to any one of <1> to <37>, wherein the total of l, m, and n, and the total of l, s, and t are each independently preferably 5 or more and 30 or less.

<41>

The compound according to any one of <1> to <37>, wherein the total of l, m, and n, and the total of l, s, and t are each independently preferably 7 or more and 25 or less.

<42>

The compound according to any one of <1> to <37>, wherein the total of l, m, and n, and the total of l, s, and t are each independently preferably 9 or more and 20 or less.

<43>

A precursor compound for producing the compound according to any one of <1> to <42>, the precursor compound being represented by a chemical formula (2) below:

[Chemical Formula (2)]

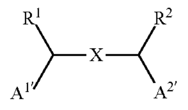

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is $—OH$, and $A^{2'}$ is $—O—CH_2—CH(OH)—CH_2OH$ or $—O—CH(—CH_2OH)_2$.

<44>

The precursor compound according to <43>, wherein $R^1$ and $R^2$ are each preferably a linear or branched alkyl group, more preferably a linear alkyl group, further preferably a linear primary alkyl group.

<45>

The precursor compound according to <43> or <44>, wherein $R^1$ and $R^2$ each independently have 1 or more and 33 or less carbon atoms.

<46>

The precursor compound according to any one of <43> to <45>, wherein $R^1$ and $R^2$ are a same aliphatic hydrocarbon group or different aliphatic hydrocarbon groups.

<47>

The precursor compound according to any one of <43> to <46>, wherein X is preferably a single bond or a hydrocarbon group having 1 or more and 3 or less carbon atoms, more preferably a single bond or a hydrocarbon group having 1 or more and 2 or less carbon atoms, further preferably a single bond or a hydrocarbon group having 1 carbon atom, still further preferably a single bond.

<48>

The precursor compound according to any one of <43> to <46>, wherein X is a single bond.

<49>

The precursor compound according to any one of <43> to <46>, wherein X is a hydrocarbon group having 1 or more and 5 or less carbon atoms.

<50>

The precursor compound according to <49>, wherein the hydrocarbon group is preferably a linear or branched alkanediyl group, more preferably a linear alkanediyl group, further preferably a linear α,ω-alkanediyl group.

<51>

The precursor compound according to any one of <43> to <50>, wherein the total number of carbon atoms of $R^1$, $R^2$, and X is preferably 10 or more, more preferably 12 or more, further preferably 14 or more, and is preferably 20 or less, more preferably 18 or less, further preferably 16 or less.

<52>

The precursor compound according to any one of <43> to <50>, wherein the total number of carbon atoms of $R^1$, $R^2$, and X is 10 or more and 20 or less.

<53>

The precursor compound according to any one of <43> to <50>, wherein the total number of carbon atoms of $R^1$, $R^2$, and X is 12 or more and 18 or less.

<54>

The precursor compound according to any one of <43> to <50>, wherein the total number of carbon atoms of $R^1$, $R^2$, and X is 14 or more and 16 or less.

<55>

The precursor compound according to any one of <43> to <54>, wherein the total number of carbon atoms of $R^1$, $R^2$, and X is even.

<56>

The precursor compound according to any one of <43> to <55>, wherein the compound represented by the chemical formula (2) includes two or more compounds that have a same total number of carbon atoms of $R^1$, $R^2$, and X, but are different in number of carbon atoms of each of $R^1$ and $R^2$.

<57>

The precursor compound according to any one of <43> to <55>, wherein the compound represented by the chemical formula (2) includes two or more compounds that have a single bond or a hydrocarbon group having 1 or more and 5 or less carbon atoms as X and a same total number of carbon atoms of $R^1$, $R^2$, and X, but are different in number of carbon atoms of each of $R^1$ and $R^2$.

<58>

The precursor compound according to any one of <43> to <55>, wherein the compound represented by the chemical formula (2) includes two or more compounds that have a single bond or a hydrocarbon group having 1 or more and 3 or less carbon atoms as X and a same total number of carbon atoms of $R^1$, $R^2$, and X, but are different in number of carbon atoms of each of $R^1$ and $R^2$.

<59>

The precursor compound according to any one of <43> to <55>, wherein the compound represented by the chemical formula (2) includes two or more compounds that have a single bond or a hydrocarbon group having 1 or more and 2 or less carbon atoms as X and a same total number of carbon atoms of $R^1$, $R^2$, and X, but are different in number of carbon atoms of each of $R^1$ and $R^2$.

<60>

The precursor compound according to any one of <43> to <55>, wherein the compound represented by the chemical formula (2) includes two or more compounds that have a single bond or a hydrocarbon group having 1 carbon atom as X and a same total number of carbon atoms of $R^1$, $R^2$, and X, but are different in number of carbon atoms of each of $R^1$ and $R^2$.

<61>

The precursor compound according to any one of <43> to <55>, wherein the compound represented by the chemical formula (2) includes two or more compounds that have a single bond as X and a same total number of carbon atoms of $R^1$, $R^2$, and X, but are different in number of carbon atoms of each of $R^1$ and $R^2$.

<62>

The precursor compound according to any one of <43> to <55>, wherein when the compound represented by the chemical formula (2) includes two or more compounds that have a single bond as X, and are different in total number of carbon atoms of $R^1$ and $R^2$, the total content of a compound having a total number of carbon atoms of $R^1$ and $R^2$ of 14 and a compound having a total number of carbon atoms of $R^1$ and $R^2$ of 16 is preferably 75 mass % or more, more preferably 85 mass % or more, further preferably 95 mass % or more, still further preferably 100 mass %.

<63>

The precursor compound according to any one of <43> to <55>, wherein when the compound represented by the chemical formula (2) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (2), preferably 10 mass % or more, more preferably 20 mass % or more, further preferably 30 mass % or more, and preferably 90 mass % or less, more preferably 80 mass % or less, further preferably 70 mass % or less.

<64>

The precursor compound according to any one of <43> to <55>, wherein when the compound represented by the chemical formula (2) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (2), 10 mass % or more and 90 mass % or less.

<65>

The precursor compound according to any one of <43> to <55>, wherein when the compound represented by the chemical formula (2) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (2), 20 mass % or more and 80 mass % or less.

<66>

The precursor compound according to any one of <43> to <55>, wherein when the compound represented by the chemical formula (2) includes two or more compounds that have a same total number of carbon atoms of $R^1$, $R^2$, and X, but are different in number of carbon atoms of each of $R^1$ and $R^2$, the content proportion of a compound in which $R^1$ has 5 or more carbon atoms and $R^2$ has 5 or more carbon atoms is, in the whole compound represented by the chemical formula (2), 30 mass % or more and 70 mass % or less.

<67>

The precursor compound according to any one of <43> to <66>, wherein when the compound represented by the chemical formula (2) is a mixed product of a compound (P1) in which $A^{1'}$ is —OH, and $A^{2'}$ is —O—$CH_2$—CH(OH)—$CH_2OH$, and a compound (P2) in which $A^{1'}$ is —OH, and $A^{2'}$ is —O—CH(—$CH_2OH)_2$, the molar proportion [P1/(P1+P2)] of P1 to the total of P1 and P2 is preferably 0.5 or more, more preferably 0.6 or more, further preferably 0.7 or more, and preferably 0.9 or less, more preferably 0.85 or less, further preferably 0.8 or less.

<68>

The precursor compound according to any one of <43> to <66>, wherein when the compound represented by the chemical formula (2) is a mixed product of a compound (P1) in which $A^{1'}$ is —OH, and $A^{2'}$ is —O—$CH_2$—CH(OH)—$CH_2OH$, and a compound (P2) in which $A^{1'}$ is —OH, and $A^{2'}$ is —O—CH(—$CH_2OH)_2$, the molar proportion [P1/(P1+P2)] of P1 to the total of P1 and P2 is 0.5 or more and 0.9 or less.

<69>

The precursor compound according to any one of <43> to <66>, wherein when the compound represented by the chemical formula (2) is a mixed product of a compound (P1) in which $A^{1'}$ is —OH, and $A^{2'}$ is —O—$CH_2$—CH(OH)—$CH_2OH$, and a compound (P2) in which $A^{1'}$ is —OH, and $A^{2'}$ is —O—CH(—$CH_2OH)_2$, the molar proportion [P1/(P1+P2)] of P1 to the total of P1 and P2 is 0.6 or more and 0.85 or less.

<70>

The precursor compound according to any one of <43> to <66>, wherein when the compound represented by the chemical formula (2) is a mixed product of a compound (P1) in which $A^{1'}$ is —OH, and $A^{2'}$ is —O—$CH_2$—CH(OH)—$CH_2OH$, and a compound (P2) in which $A^{1'}$ is —OH, and $A^{2'}$ is —O—CH(—$CH_2OH)_2$, the molar proportion [P1/(P1+P2)] of P1 to the total of P1 and P2 is 0.7 or more and 0.8 or less.

<71>

A surfactant composition containing the compound according to any one of <1> to <42>.

<72>

The surfactant composition according to <71>, wherein the content of the compound represented by the chemical formula (1) in the surfactant composition is preferably 50 mass % or more, more preferably 60 mass % or more, further preferably 70 mass % or more, still further preferably 80 mass % or more, and is preferably 99 mass % or less, more preferably 95 mass % or less, further preferably 90 mass % or less.

<73>

The surfactant composition according to <71>, wherein the content of the compound represented by the chemical formula (1) in the surfactant composition is 50 mass % or more and 99 mass % or less.

<74>

The surfactant composition according to <71>, wherein the content of the compound represented by the chemical formula (1) in the surfactant composition is 60 mass % or more and 95 mass % or less.

<75>

The surfactant composition according to <71>, wherein the content of the compound represented by the chemical formula (1) in the surfactant composition is 70 mass % or more and 90 mass % or less.

<76>

The surfactant composition according to <71>, wherein the content of the compound represented by the chemical formula (1) in the surfactant composition is 80 mass % or more and 90 mass % or less.

<77>

The surfactant composition according to any one of <71> to <76>, wherein the surfactant composition contains water.

<78>

The surfactant composition according to <77>, wherein the water is preferably purified water, and more preferably ion-exchanged water, distilled water, or reverse osmosis water.

<79>

The surfactant composition according to <77> or <78>, wherein the content of the water in the surfactant composition is 1 mass % or more, 5 mass % or more, or 10 mass % or more, and 50 mass % or less, 40 mass % or less, 30 mass % or less, or 20 mass % or less.

<80>

The surfactant composition according to any one of <71> to <79>, wherein the surfactant composition contains a surfactant different from the compound represented by the chemical formula (1), or a solvent.

<81>

The surfactant composition according to <80>, wherein the content of the solvent in the surfactant composition is preferably 10 mass % or less, more preferably 4 mass % or less, further preferably 1 mass % or less, still further preferably 0.1 mass % or less.

<82>

The surfactant composition according to any one of <71> to <81>, wherein the surfactant composition is an emulsifier composition, a wetting agent composition, or a penetrant composition.

<83>

A detergent composition containing the compound according to any one of <1> to <42>.

<84>

The detergent composition according to <83>, wherein the content of the compound represented by the chemical formula (1) in the detergent composition is preferably 0.1 mass % or more, more preferably 1 mass % or more, further preferably 10 mass % or more, still further preferably 30 mass % or more, still further preferably 40 mass % or more, and is preferably 99 mass % or less, more preferably 90 mass % or less, further preferably 80 mass % or less.

<85>

The detergent composition according to <83>, wherein the content of the compound represented by the chemical formula (1) in the detergent composition is 0.1 mass % or more and 99 mass % or less.

<86>

The detergent composition according to <83>, wherein the content of the compound represented by the chemical formula (1) in the detergent composition is 1 mass % or more and 90 mass % or less.

<87>

The detergent composition according to <83>, wherein the content of the compound represented by the chemical formula (1) in the detergent composition is 10 mass % or more and 80 mass % or less.

<88>

The detergent composition according to <83>, wherein the content of the compound represented by the chemical formula (1) in the detergent composition is 30 mass % or more and 80 mass % or less.

<89>

The detergent composition according to <83>, wherein the content of the compound represented by the chemical formula (1) in the detergent composition is 40 mass % or more and 80 mass % or less.

<90>

The detergent composition according to any one of <83> to <89>, wherein the detergent composition contains a surfactant different from the compound represented by the chemical formula (1).

<91>

The detergent composition according to any one of <83> to <90>, wherein the detergent composition contains water.

<92>

The detergent composition according to <91>, wherein the water is preferably purified water, and more preferably ion-exchanged water, distilled water, or reverse osmosis water.

<93>

The detergent composition according to <91> or <92>, wherein the content of the water in the detergent composition is 1 mass % or more, 10 mass % or more, 20 mass % or more, 30 mass % or more, 40 mass % or more, 50 mass % or more, and 99.5 mass % or less, 90 mass % or less, 70 mass % or less, 60 mass % or less, 50 mass % or less, 40 mass % or less, 30 mass % or less, 20 mass % or less, 10 mass % or less, 5 mass % or less.

<94>

The detergent composition according to any one of <83> to <93>, wherein the detergent composition contains a solvent.

<95>

The detergent composition according to <94>, wherein the content of the solvent in the detergent composition is preferably 10 mass % or less, more preferably 4 mass % or less, further preferably 1 mass % or less, still further preferably 0.1 mass % or less.

<96>

Use of the precursor compound represented by a chemical formula (2) below, for producing the compound according to any one of <1> to <42>:

[Chemical Formula (2)]

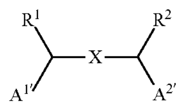

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is —OH, and $A^{2'}$ is —O—$CH_2$—CH(OH)—$CH_2$OH or —O—CH(—$CH_2$OH)$_2$.

<97>

A method for producing the compound according to any one of <1> to <42>, including a process of adding an alkylene oxide having 2 or more and 8 or less carbon atoms to a precursor compound represented by the chemical formula (2) below:

[Chemical Formula (2)]

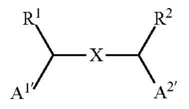

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is —OH, and $A^{2'}$ is —O—$CH_2$—CH(OH)—$CH_2$OH or —O—CH(—$CH_2$OH)$_2$.

EXAMPLES

Hereinafter, the present invention is specifically described on the basis of examples. The content of the components in tables is represented in mass % unless otherwise described. The measurement methods are as follows.

<Method for Measuring Position of Double Bond in Internal Olefin>

The position of a double bond in a prepared internal olefin was measured by gas chromatography (hereinafter, abbreviated as GC). Specifically, the internal olefin was reacted with dimethyl sulfide into a dithionate derivative, and the components were then separated by GC. The position of a double bond in the internal olefin was obtained from the peak areas of the components. The apparatus used for the measurement and the analysis conditions are as follows.

GC apparatus: trade name HP6890 (manufactured by Hewlett-Packard Company)

Column: trade name Ultra-Alloy-1HT capillary column 30 m×250 μm×0.15 μm (manufactured by Frontier Laboratories Ltd.)

Detector: hydrogen flame ion detector (FID)

Injection temperature: 300° C.

Detector temperature: 350° C.

Oven: 60° C. (0 min.)→2° C./min.→225° C.→20° C./min.→350° C.→350° C. (5.2 min.)

<Method for Measuring Content Proportion of Structural Isomer>

A mixture of 0.05 g of alkyl glyceryl ether, 0.2 g of trifluoroacetic anhydride, and 1 g of deuterated chloroform was measured by $^1$H-NMR. The measurement conditions are as follows.

Nuclear magnetic resonance apparatus: Agilent 400-MR DD2, manufactured by Agilent Technologies, Inc.

Observation range: 6410.3 Hz

Data point: 65536

Measurement mode: Presat

Pulse width: 45°

Pulse delay time: 10 sec

Cumulated number: 128 times

Production of Internal Olefin

Production Example A1

(Production of Internal Olefin (Internal Olefin 1) having 16 Carbon Atoms)

Into a flask equipped with a stirrer were charged 7000 g (28.9 mol) of 1-hexadecanol (product name: KALCOL 6098, manufactured by Kao Corporation) and 700 g (10 wt % relative to raw material alcohol) of γ-alumina (STREM Chemicals, Inc.) as a solid acid catalyst, and the mixture was reacted under stirring at 280° C. for 32 hours with a flow of nitrogen (7000 mL/min) through the system. After the completion of the reaction, the alcohol conversion rate was 100% and the C16 olefin purity was 99.6%. The obtained crude C16 internal olefin was transferred to a distiller, and was distilled at 136 to 160° C./4.0 mmHg to give an internal olefin 1 having an olefin purity of 100%. The double bond distribution in the obtained internal olefin 1 was 0.2% at the C1 position, 15.8% at the C2 position, 14.5% at the C3 position, 15.7% at the C4 position, 17.3% at the C5 position, 16.5% at the C6 position, and 20.0% at the C7 position and the C8 position in total.

Production Example A2

(Production of Internal Olefin (Internal Olefin 2) having 18 Carbon Atoms)

Into a reactor equipped with a stirrer were charged 800 kg (3.0 kmol) of 1-octadecanol (product name: KALCOL 8098, manufactured by Kao Corporation) and 80 kg (10 wt % relative to raw material alcohol) of activated alumina GP-20 (Mizusawa Industrial Chemicals, Ltd.) as a solid acid catalyst, and the mixture was reacted under stirring at 280° C. for 16 hours with a flow of nitrogen (15 L/min) through the system. After the completion of the reaction, the alcohol conversion rate was 100% and the C18 olefin purity was 98.7%. The obtained crude C18 internal olefin was transferred to a distiller, and was distilled at 163 to 190° C./4.6 mmHg to give an internal olefin 2 having an olefin purity of 100%. The double bond distribution in the obtained internal olefin 2 was 0.3% at the C1 position, 13.3% at the C2 position, 12.6% at the C3 position, 13.9% at the C4 position, 14.8% at the C5 position, 13.7% at the C6 position, 12.6 at the C7 position, and 18.8% at the C8 position and the C9 position in total.

Production of Internal Epoxide

Production Example B1

(Production of Internal Epoxide (Internal Epoxide 1) having 16 Carbon Atoms)

Into a flask equipped with a stirrer were charged 800 g (3.56 mol) of the internal olefin 1 obtained in Production Example A1, 107 g (1.78 mol) of acetic acid (manufactured by Wako Pure Chemical Industries, Ltd.), 15.6 g (0.15 mol) of sulfuric acid (manufactured by Wako Pure Chemical Industries, Ltd.), 415.7 g (4.28 mol) of 35% hydrogen peroxide (manufactured by Wako Pure Chemical Industries, Ltd.), and 25.3 g (0.18 mol) of sodium sulfate (manufactured by Wako Pure Chemical Industries, Ltd.), and the mixture was reacted at 50° C. for 4 hours. Thereafter, the mixture was heated to 70° C. and further reacted for 2 hours. After the reaction, the mixture was separated into layers, an aqueous layer was removed, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and 1% saline (manufactured by Wako Pure Chemical Industries, Ltd.), and concentrated in an evaporator to give 820 g of an internal epoxide 1.

Production Example B2

(Production of Internal Epoxide (Internal Epoxide 2) having 18 Carbon Atoms)

Into a flask equipped with a stirrer were charged 595 g (2.38 mol) of the internal olefin 2 obtained in Production Example A2, 71.7 g (1.20 mol) of acetic acid (manufactured by Wako Pure Chemical Industries, Ltd.), 9.8 g (0.10 mol) of sulfuric acid (manufactured by Wako Pure Chemical Industries, Ltd.), and 324 g (4.00 mol) of 35% hydrogen peroxide (manufactured by Wako Pure Chemical Industries, Ltd.), and the mixture was reacted at 50° C. for 4 hours. Thereafter, the mixture was heated to 80° C. and further reacted for 5 hours. After the reaction, the mixture was separated into layers, an aqueous layer was removed, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and ion-exchanged water, and concentrated in an evaporator to give 629 g of an internal epoxide 2.

<Production of Reactant (Alkyl Glyceryl Ether, AGE) of Internal Epoxide and Glycerin)

Hereinafter, an alkyl glyceryl ether is described as an AGE. The AGE 1, the AGE 2 and the like represent an alkyl glyceryl ether 1, an alkyl glyceryl ether 2, and the like, respectively.

Production Example C1

(Production of Reactant (AGE 1) of Internal Epoxide 1 and Glycerin)

Into a flask equipped with a stirrer were charged 2298 g (25.0 mol) of glycerin (manufactured by Wako Pure Chemical Industries, Ltd.) and 0.122 g (1.25 mmol) of 98% sulfuric acid (manufactured by Wako Pure Chemical Industries, Ltd.), and the mixture was heated to 130° C. Thereafter, 300 g (1.25 mol) of the internal epoxide 1 obtained in Production Example B1 were added dropwise over 1 hour, and the mixture was reacted at 130° C./8 hours. Hexane was added to the liquid obtained by this reaction, and the mixture was washed with ion-exchanged water and then concentrated under reduced pressure in an evaporator to give 400 g of an AGE 1. The obtained AGE 1 contained 73% of ether alcohol (AGE obtained through a reaction of a hydroxy group at the 1-position of glycerin with an epoxy group) in which $R^1$ and $R^2$ each independently included an alkyl group having 1 to 13 carbon atoms, the total number of carbon atoms of $R^1$ and $R^2$ was 14, X was a single bond, either one of $A^{1'}$ or $A^{2'}$ was $—OH$ and the other is $—O—CH_2—CH(OH)—CH_2OH$ or $—O—CH(—CH_2—OH)_2$, and $A^{1'}$ or $A^{2'}$ was $—O—CH_2—CH(OH)—CH_2OH$ in the chemical formula (2), and 27% of ether alcohol (AGE obtained through a reaction of a hydroxy group at the 2-position of glycerin with an epoxy group) in which $A^{1'}$ or $A^{2'}$ was $—O—CH(—CH_2—OH)_2$.

Production Example C2

(Production of Reactant (AGE 2) of Internal Epoxide 2 and Glycerin)

An AGE 2 was obtained by the same production method as in Production Example C1 except that the internal epoxide 2 (1.25 mol) obtained in Production Example B2 was used in place of the internal epoxide 1 (1.25 mol) obtained in Production Example B1. The obtained AGE 2 contained 72% of an AGE obtained through a reaction of a hydroxy group at the 1-position of glycerin with an epoxy group, in which $R^1$ and $R^2$ each independently included an alkyl group having 1 to 15 carbon atoms, the total number of carbon atoms of $R^1$ and $R^2$ was 16, X was a single bond, and either one of $A^{1'}$ or $A^{2'}$ was —OH and the other is —O—$CH_2$—CH(OH)—$CH_2$OH or —O—CH(—$CH_2$—$OH)_2$ in the chemical formula (2), and 28% of an AGE obtained through a reaction of a hydroxy group at the 2-position of glycerin with an epoxy group.

Production of Internal Three Hydrophilic Groups-Containing Compound

Production Example 1

(Production of EO (9 mol) Adduct of AGE 1 (Example Product 1))

Into a 2-L autoclave equipped with a stirrer, a thermometer, and an AO inlet tube were charged 200 g (0.601 mol, raw material) of the AGE 1 obtained in Production Example C1 and 0.675 g (0.0120 mol) of 86% KOH, and after nitrogen substitution was performed, the mixture was subjected to dehydration at 110° C. and −0.101 MPa for 1 hour. Thereafter, 239 g (5.41 mol) of EO (ethylene oxide) was fed to the mixture and thus added at an initial nitrogen pressure of 0.005 MPa and 155±5° C. Thereafter, 0.722 g (0.0120 mol) of acetic acid was added and the mixture was thereby neutralized to give an example product 1. The average number of added moles of EO in the obtained product was confirmed by $^1$H-NMR.

Production Example 2

(Production of EO (14 mol) Adduct of AGE 1 (Example Product 2))

An example product 2 was obtained by the same production method as in Production Example 1 except for changing the feeding amount of EO to 372 g (8.41 mol). The average number of added moles of EO in the obtained product was confirmed by $^1$H-NMR.

Production Example 3

(Production of EO (5 mol) Adduct of AGE 2 (Example Product 3))

An example product 3 was obtained by the same production method as in Production Example 1 except that the AGE 2 obtained in Production Example C2 was used in place of the AGE 1 obtained in Production Example C1 and 5 mol of EO were fed to 1 mol of the AGE 2. The average number of added moles of EO in the obtained product was confirmed by $^1$H-NMR.

Production Example 4

(Production of EO (7 mol) Adduct of AGE 2 (Example Product 4))

An example product 4 was obtained by the same production method as in Production Example 3 except that 7 mol of EO were fed to 1 mol of the AGE 2. The average number of added moles of EO in the obtained product was confirmed by $^1$H-NMR.

Production Example 5

(Production of EO (9 mol) Adduct of AGE 2 (Example Product 5))

An example product 5 was obtained by the same production method as in Production Example 3 except that 9 mol of EO were fed to 1 mol of the AGE 2. The average number of added moles of EO in the obtained product was confirmed by $^1$H-NMR.

Production Example 6

(Production of EO (3 mol) and PO (5.4 mol) Adduct of AGE 2 (Example Product 6))

An example product 6 was obtained by the same production method as in Production Example 3 except that after 3 mol of EO were fed to 1 mol of the AGE 2, 5.4 mol of PO (propylene oxide) were fed to the 1 mol of the AGE 2. The average numbers of added moles of EO and PO in the obtained product were confirmed by $^1$H-NMR.

Production Example 7

(Production of EO (5 mol) and PO (9 mol) Adduct of AGE 2 (Example Product 7))

An example product 7 was obtained by the same production method as in Production Example 3 except that after 5 mol of EO were fed to 1 mol of the AGE 2, 9 mol of PO were fed to the 1 mol of the AGE 2. The average numbers of added moles of EO and PO in the obtained product were confirmed by $^1$H-NMR.

Production Example 8

(Production of EO (7 mol) and PO (12.6 mol) Adduct of AGE 2 (Example Product 8))

An example product 8 was obtained by the same production method as in Production Example 3 except that after 7 mol of EO were fed to 1 mol of the AGE 2, 12.6 mol of PO were fed to the 1 mol of the AGE 2. The average numbers of added moles of EO and PO in the obtained product were confirmed by $^1$H-NMR.

Production Example 9

(Production of EO (5 mol) Adduct of AGE 1 (Example Product 9))

An example product 9 was obtained by the same production method as in Production Example 1 except that 5 mol of EO were fed to 1 mol of the AGE 1. The average number of added moles of EO in the obtained product was confirmed by $^1$H-NMR.

Production Example 10

(Production of EO (7 mol) Adduct of AGE 1 (Example Product 10))

An example product 10 was obtained by the same production method as in Production Example 1 except that 7 mol of EO were fed to 1 mol of the AGE 1. The average number of added moles of EO in the obtained product was confirmed by $^1$H-NMR.

Production Example 11

(Production of EO (4 mol) Adduct of AGE 2 (Example Product 11))

An example product 11 was obtained by the same production method as in Production Example 3 except that 4 mol of EO were fed to 1 mol of the AGE 2. The average number of added moles of EO in the obtained product was confirmed by $^1$H-NMR.

Production Example 12

(Production of PO (3 mol) and EO (5 mol) Adduct of AGE 2 (Example Product 12))

An example product 12 was obtained by the same production method as in Production Example 3 except that after 3 mol of PO were fed to 1 mol of the AGE 2, 5 mol of EO were fed to the 1 mol of the AGE 2. The average numbers of added moles of EO and PO in the obtained product were confirmed by $^1$H-NMR.

Production Example 13

(Production of EO (5.4 mol) and PO (3 mol) adduct of AGE 2 (Example Product 13))

An example product 13 was obtained by the same production method as in Production Example 3 except that after 5.4 mol of EO were fed to 1 mol of the AGE 2, 3 mol of PO were fed to the 1 mol of the AGE 2. The average numbers of added moles of EO and PO in the obtained product were confirmed by $^1$H-NMR.

Production Example 14

(Production of EO (14 mol) Adduct of AGE 2 (Example Product 14))

An example product 14 was obtained by the same production method as in Production Example 3 except that 14 mol of EO were fed to 1 mol of the AGE 2. The average number of added moles of EO in the obtained product was confirmed by $^1$H-NMR.

Table 1 shows the example products 1 to 14 with the details of the chemical formula (1).

Production Example 15

(Production of Polyoxyethylene(10) Alkyl (Lauryl and Myristyl Mixed) Ether (Comparative Product 1))

A comparative product 1 was obtained by a normal method, that is, adding 10 mol of EO (ethylene oxide) to mixed alcohol of lauryl alcohol (manufactured by Kao Corporation, KALCOL 2098) and myristyl alcohol (manufactured by Kao Corporation, KALCOL 4098) (mass ratio 72:28). The average number of added moles of EO in the obtained product was confirmed by $^1$H-NMR.

Comparative Product 2

(Polyoxyethylene(7) alkyl (secondary dodecyl and secondary tetradecyl mixed) ether (NIPPON SHOKUBAI CO., LTD., SOFTANOL 70) was used as a comparative product 2.

Comparative Product 3

(Polyoxyethylene(9) alkyl (secondary dodecyl and secondary tetradecyl mixed) ether (NIPPON SHOKUBAI CO., LTD., SOFTANOL 90) was used as a comparative product 3.

Table 1 shows the example products 1 to 14.

TABLE 1

| | | | | | Details of chemical formula (1) | | | | |
|---|---|---|---|---|---|---|---|---|---|
| Example product | Production Example | AGE | EO (mol) | PO (mol) | Number of carbon atoms of each of $R^1$ and $R^2$ | Total number of carbon atoms of $R^1$ and $R^2$ | X | $A^{11}$, $A^{21}$, $A^{22}$, $A^{23}$, and $A^{24}$ | Total of l, m, and n or total of l, s, and t (average value) |
| Example product 9 | Production Example 9 | AGE 1 | 5 | — | 1 to 13 | 14 | Single bond | Ethanediyl group | 5 |
| Example product 10 | Production Example 10 | AGE 1 | 7 | — | 1 to 13 | 14 | Single bond | Ethanediyl group | 7 |
| Example product 1 | Production Example 1 | AGE 1 | 9 | — | 1 to 13 | 14 | Single bond | Ethanediyl group | 9 |
| Example product 2 | Production Example 2 | AGE 1 | 14 | — | 1 to 13 | 14 | Single bond | Ethanediyl group | 14 |
| Example product 11 | Production Example 11 | AGE 2 | 4 | — | 1 to 15 | 16 | Single bond | Ethanediyl group | 4 |
| Example product 3 | Production Example 3 | AGE 2 | 5 | — | 1 to 15 | 16 | Single bond | Ethanediyl group | 5 |
| Example product 4 | Production Example 4 | AGE 2 | 7 | — | 1 to 15 | 16 | Single bond | Ethanediyl group | 7 |
| Example product 5 | Production Example 5 | AGE 2 | 9 | — | 1 to 15 | 16 | Single bond | Ethanediyl group | 9 |
| Example product 14 | Production Example 14 | AGE 2 | 14 | — | 1 to 15 | 16 | Single bond | Ethanediyl group | 14 |
| Example product 6 | Production Example 6 | AGE 2 | 3 | 5.4 | 1 to 15 | 16 | Single bond | Ethanediyl group or 1,2-propanediyl group | 8.4 |
| Example product 7 | Production Example 7 | AGE 2 | 5 | 9 | 1 to 15 | 16 | Single bond | Ethanediyl group or 1,2-propanediyl group | 14 |

TABLE 1-continued

| | | | | | Details of chemical formula (1) | | | | |
|---|---|---|---|---|---|---|---|---|---|
| Example product | Production Example | AGE | EO (mol) | PO (mol) | Number of carbon atoms of each of $R^1$ and $R^2$ | Total number of carbon atoms of $R^1$ and $R^2$ | X | $A^{11}$, $A^{21}$, $A^{22}$, $A^{23}$, and $A^{24}$ | Total of 1, m, and n or total of 1, s, and t (average value) |
| Example product 8 | Production Example 8 | AGE 2 | 7 | 12.6 | 1 to 15 | 16 | Single bond | Ethanediyl group or 1,2-propanediyl group | 19.6 |
| Example product 12 | Production Example 12 | AGE 2 | 5 | 3 | 1 to 15 | 16 | Single bond | Ethanediyl group or 1,2-propanediyl group | 8 |
| Example product 13 | Production Example 13 | AGE 2 | 5.4 | 3 | 1 to 15 | 16 | Single bond | Ethanediyl group or 1,2-propanediyl group | 8.4 |

Evaluation of Low-Concentration Detergency

Example 1 (Examples 1-1 to 1-8 and Comparative Example 1-1)

The example products and the comparative product shown in Table 2 were evaluated for the detergency by the following method. Table 2 shows the results.

TABLE 2

| | | Detergency rate (GIV) (%) |
|---|---|---|
| Example 1-1 | Example product 1 | 58.9 |
| Example 1-2 | Example product 2 | 42.8 |
| Example 1-3 | Example product 3 | 36.6 |
| Example 1-4 | Example product 4 | 46.0 |
| Example 1-5 | Example product 5 | 51.2 |
| Example 1-6 | Example product 6 | 38.3 |
| Example 1-7 | Example product 7 | 44.5 |
| Example 1-8 | Example product 8 | 39.0 |
| Comparative Example 1-1 | Comparative product 1 | 48.7 |

[Preparation of Model-Sebum Artificially Soiled Fabric]

Model-sebum artificially soiled fabric was prepared by applying a model-sebum artificially soiling liquid having the following composition to fabric (cotton 2003 (manufactured by Senshoku shizai K. K. Tanigashira shouten)). The application of the model-sebum artificially soiling liquid to the fabric was carried out by performing gravure-roll-coater printing on the fabric with the artificially soiling liquid. The step of applying the model-sebum artificially soiling liquid to the fabric and thus preparing the model-sebum artificially soiled fabric was performed at a gravure-roll cell volume of 58 $cm^3/m^2$, an application rate of 1.0 m/min, a drying temperature of 100° C., and a drying time of 1 min. Thereafter, the fabric was cut into a size of 6 cm×6 cm.

The composition of the model-sebum artificially soiling liquid: 0.4 mass % of lauric acid, 3.1 mass % of myristic acid, 2.3 mass % of pentadecanoic acid, 6.2 mass % of palmitic acid, 0.4 mass % of heptadecanoic acid, 1.6 mass % of stearic acid, 7.8 mass % of oleic acid, 13.0 mass % of triolein, 2.2 mass % of n-hexadecyl palmitate, 6.5 mass % of squalene, 1.9 mass % of egg-white lecithin liquid crystal, 8.1 mass % of Kanuma red soil, 0.01 mass % of carbon black, and the balance water (total 100 mass %)

[Washing Test]

The washing operation was performed using a tergotometer (manufactured by Ueshima Seisakusho Co., Ltd.). Washing water was obtained by charging calcium chloride and magnesium chloride at a mass ratio of 8:2 into ion-exchanged water and adjusting the hardness of the mixture to 4° dH (see JP-A-2017-214570 for the method for measuring German hardness). A washing liquid was obtained by mixing the example product or the comparative product shown in Table 2 with the washing water so that the concentration of the washing liquid was 50 ppm. Into a 1-L washing test stainless-steel beaker were charged 0.6 L of the washing liquid and 5 pieces of the model-sebum artificially soiled fabric. The temperature of the washing liquid was 20° C. The model-sebum artificially soiled fabric was washed by the tergotometer at 85 rpm for 10 minutes. After the washing, the fabric was dehydrated and dried for 24 hours in an environment of 23° C. and 45% RH.

The detergency rate (%) of the model-sebum artificially soiled fabric was measured by the following method, and the average value of the 5 pieces of the fabric was obtained. Table 1 shows the results. The reflectance at 550 nm of unsoiled original fabric and the soiled fabric before and after washing was measured by a chromometer (manufactured by NIPPON DENSHOKU INDUSTRIES CO., LTD., Z-300A), and the detergency rate (%) was obtained by the following equation.

$$\text{Detergency rate (\%)}=100\times[(\text{reflectance after washing}-\text{reflectance before washing})/(\text{reflectance of original fabric}-\text{reflectance before washing})]$$

Evaluation of Foaming

Example 2 (Examples 2-1 to 2-6 and Comparative Examples 2-1 to 2-3)

The example product or the comparative product shown in Table 3 in an amount of 1.5 g was placed in a 500-mL beaker, an appropriate amount of ion-exchanged water was added into the beaker, and the mixture was heated to 60° C. to give a uniform aqueous solution. Then, the aqueous solution was replenished with ion-exchanged water to prepare a surfactant composition having a concentration of 0.5 mass %. The prepared surfactant composition was heated to 60° C., stirred and uniformized, and then measured for the height (cm) of foam after 0 minutes, 1 minute, 2 minutes, 3 minutes, 4 minutes, and 5 minutes on the basis of the test method of synthetic detergent (Ross-Miles Method) of JIS K 3362 (2008). Table 3 shows the results. The smaller the value of the foam height is, the more excellent the defoaming properties are.

TABLE 3

| | | Height of foam (cm) | | | | | |
|---|---|---|---|---|---|---|---|
| | | After 0 min | After 1 min | After 2 min | After 3 min | After 4 min | After 5 min |
| Example 2-1 | Example product 4 | 16.0 | 12.9 | 10.9 | 6.0 | 2.0 | 2.0 |
| Example 2-2 | Example product 5 | 15.3 | 11.3 | 2.6 | 0.9 | 0.6 | 0.6 |
| Example 2-3 | Example product 14 | 18.8 | 15.1 | 7.2 | 1.5 | 0.9 | 0.7 |
| Example 2-4 | Example product 6 | 2.0 | 1.1 | 0.8 | 0.8 | 0.7 | 0.7 |
| Example 2-5 | Example product 7 | 4.4 | 0.8 | 0.8 | 0.8 | 0.7 | 0.6 |
| Example 2-6 | Example product 8 | 6.5 | 0.6 | 0.6 | 0.6 | 0.6 | 0.6 |
| Comparative Example 2-1 | Comparative product 1 | 18.8 | 17.8 | 17.7 | 17.5 | 17.4 | 17.4 |
| Comparative Example 2-2 | Comparative product 2 | 18.0 | 16.4 | 15.7 | 15.2 | 14.8 | 14.0 |
| Comparative Example 2-3 | Comparative product 3 | 20.2 | 18.8 | 18.4 | 17.8 | 17.3 | 16.4 |

Evaluation of Penetrativeness

Example 3 (Examples 3-1 to 3-8 and Comparative Example 3-1)

Into a 100-mL beaker were poured 50 mL of an aqueous surfactant solution (20° C.) containing 0.1 mass % of the example product or the comparative product shown in Table 4, and the aqueous solution had foam removed from the surface thereof with a dropper and was left to stand still for 3 minutes. The time was measured from when cotton canvas (gray fabric, stocking stitch, 2.0×2.0 cm) was gently floated on the aqueous solution with tweezers until the cotton canvas was completely sunk below the surface of water. The measurement was performed 5 times in total, with the aqueous surfactant solution changed, and the average value thereof was defined as a sinking time (s). Table 4 shows the results. The value of the sinking time is smaller, the more excellent penetrativeness is.

TABLE 4

| | | Sinking time (s) |
|---|---|---|
| Example 3-1 | Example product 9 | 25 |
| Example 3-2 | Example product 10 | 119 |
| Example 3-3 | Example product 11 | 142 |
| Example 3-4 | Example product 3 | 52 |
| Example 3-5 | Example product 12 | 28 |
| Example 3-6 | Example product 6 | 25 |
| Example 3-7 | Example product 7 | 35 |
| Example 3-8 | Example product 13 | 53 |
| Comparative Example 3-1 | Comparative product 1 | 300< |

Evaluation of Emulsifiability

Example 4 (Examples 4-1 to 4-25 and Comparative Examples 4-1 to 4-4)

Into a glass 50-mL sample bottle were poured 0.5 g of the example product (but none used in Comparative Examples 4-1 to 4-4) shown in Table 5, 10 mL of ion-exchanged water, and 10 mL each of the oils, the mixture was shaken for 30 seconds, and one liquid droplet was then placed on slide glass and held with cover glass, and observed with digital microscope VHX-6000 (manufactured by KEYENCE CORPORATION) at 500-fold magnification. The particle size of the liquid droplet was measured and evaluated according to the following criteria. Table 5 shows the results.

1: average particle size of less than 1 μm
2: average particle size of 1 to 100 μm
3: average particle size of more than 100 μm
4: separated and no liquid droplet observed

TABLE 5

| emulsifiability | | | |
|---|---|---|---|
| | | Oil | Evaluation of emulsifiability |
| Example 4-1 | Example product 9 | Decane | 2 |
| Example 4-2 | | Oleic acid | 2 |
| Example 4-3 | | Triolein | 3 |
| Example 4-4 | Example product 10 | Decane | 2 |
| Example 4-5 | | Toluene | 1 |
| Example 4-6 | | Triolein | 3 |
| Example 4-7 | Example product 2 | Decane | 2 |
| Example 4-8 | | Toluene | 2 |
| Example 4-9 | | Oleic acid | 2 |
| Example 4-10 | | Triolein | 3 |
| Example 4-11 | Example product 3 | Decane | 2 |
| Example 4-12 | | Toluene | 1 |
| Example 4-13 | | Oleic acid | 2 |
| Example 4-14 | | Triolein | 3 |
| Example 4-15 | Example product 4 | Decane | 2 |
| Example 4-16 | | Toluene | 1 |
| Example 4-17 | | Triolein | 3 |
| Example 4-18 | Example product 5 | Decane | 2 |
| Example 4-19 | | Toluene | 2 |
| Example 4-20 | | Oleic acid | 2 |
| Example 4-21 | | Triolein | 3 |
| Example 4-22 | Example product 14 | Decane | 3 |
| Example 4-23 | | Toluene | 2 |
| Example 4-24 | | Oleic acid | 2 |
| Example 4-25 | | Triolein | 3 |
| Comparative Example 4-1 | — | Decane | 4 |
| Comparative Example 4-2 | | Toluene | 4 |
| Comparative Example 4-3 | | Oleic acid | 4 |
| Comparative Example 4-4 | | Triolein | 4 |

Evaluation of Wettability

Example 5 (Examples 5-1 to 5-9 and Comparative Examples 5-1 and 5-2)

Slide grass (76 mm×26 mm×1 mm) as a glass substrate, and a polypropylene substrate (80 mm×30 mm×1 mm) (PP substrate) were used. The glass substrate or the PP substrate was horizontally set on a stage of a contact angle meter (manufactured by Kyowa Interface Science Co., Ltd., DM-701), and 2 μL of a 1 mass % aqueous solution of the example product shown in Table 6 was dropped with a syringe on the set substrate and measured for the contact angle after 10 seconds. Table 6 shows the results. For Comparative Examples 5-1 and 5-2 in Table 6, ion-exchanged water was used in place of the aqueous solution, and the contact angle was measured in the same manner. Table 6 shows the results.

TABLE 6

| | | Substrate | Contact angle (°) |
|---|---|---|---|
| Example 5-1 | Example product 9 | Glass | <1 |
| Example 5-2 | Example product 10 | Glass | <1 |
| Example 5-3 | Example product 2 | Glass | <1 |
| Example 5-4 | Example product 3 | Glass | <1 |
| Example 5-5 | Example product 4 | Glass | <1 |
| Example 5-6 | Example product 5 | Glass | <1 |
| Example 5-7 | Example product 14 | Glass | <1 |
| Example 5-8 | Example product 9 | PP | 29 |
| Example 5-9 | Example product 10 | PE | 40 |
| Comparative Example 5-1 | — | Glass | 9 |
| Comparative Example 5-2 | — | PP | 97 |

Evaluation of Dispersibility

Example 6 (Examples 6-1 to 6-5 and Comparative Example 6-1)

Into a 50-mL screw tube were poured a total 30 g of carbon black (MA-100, manufactured by Mitsubishi Chemical Corporation), the example product (none in Comparative Example 6-1), and ion-exchanged water at the ratio shown in Table 7. The screw tube was shaken for 30 seconds and the appearance thereof was observed after 10 minutes. Table 7 shows the results. In all of Examples 6-1 to 6-5, the appearance was uniform and the dispersibility was good. In Comparative Example 6-1, the carbon black was precipitated and separated, and the dispersibility was poor.

TABLE 7

| | | Example 6-1 | Example 6-2 | Example 6-3 | Example 6-4 | Example 6-5 | Comparative Example 6-1 |
|---|---|---|---|---|---|---|---|
| Content [mass %] | Example product 3 | 2 | | | | | |
| | Example product 4 | | 2 | | | | |
| | Example product 5 | | | 2 | | | |
| | Example product 14 | | | | 2 | | |
| | Example product 7 | | | | | 2 | |
| | Carbon black | 5 | 5 | 5 | 5 | 5 | 5 |
| | Water | Balance | Balance | Balance | Balance | Balance | Balance |
| | Total | 100 | 100 | 100 | 100 | 100 | 100 |
| Appearance after 10 min | | Uniform | Uniform | Uniform | Uniform | Uniform | Separated |

INDUSTRIAL APPLICABILITY

The surfactant composition and the detergent composition according to the present invention are useful as detergents for various uses.

The invention claimed is:

1. A compound represented by a chemical formula (1) below:

[Chemical Formula (1)]

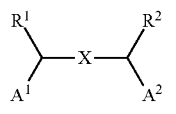

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^1$ is $—O(-A^{11}O)_t—H$, $A^2$ is $O—CH_2—CH(—O(-A^{21}O)_m—H)(—CH_2—O(-A^{22}O)_n—H)$ or $—O—CH(—CH_2—O(-A^{23}O)_s—H)(—CH_2—O(-A^{24}O)_t—H)$, $A^{11}$, $A^{21}$, $A^{22}$, $A^{23}$, and $A^{24}$ are each independently an alkanediyl group having 2 or more and 8 or less carbon atoms, l, m, n, s, and t are an average value and are each independently 0 or more, and a total of l, m, and n, and a total of l, s, and t are each independently more than 0 and 200 or less.

2. The compound according to claim 1, wherein X is a single bond in the compound represented by the chemical formula (1).

3. The compound according to claim 1, wherein $A^{11}$, $A^{21}$, $A^{22}$, $A^{23}$, and $A^{24}$ in the chemical formula (1) are each independently an alkanediyl group having 2 or 3 carbon atoms.

4. The compound according to claim 1, wherein the compound represented by the chemical formula (1) comprises two or more compounds that have a same total number of carbon atoms of $R^1$, $R^2$, and X, but are different in number of carbon atoms of each of $R^1$ and $R^2$.

5. The compound according to claim 1, wherein the total number of carbon atoms of $R^1$, $R^2$, and X is 10 or more and 20 or less.

6. The compound according to claim 1, wherein $R^1$ and $R^2$ are each a linear or branched alkyl group.

7. A surfactant composition comprising the compound according to claim 1.

8. The surfactant composition according to claim 7, the composition being an emulsifier composition, a wetting agent composition, or a penetrant composition.

9. A detergent composition comprising the compound according to claim 1.

10. The detergent composition according to claim 9, wherein a content of the compound represented by the chemical formula (1) in the detergent composition is 0.1 mass % or more and 99 mass % or less.

11. The compound according to claim 1, wherein the compound represented by the chemical formula (1) comprises two or more compounds that have a single bond as X and a same total number of carbon atoms of $R^1$, $R^2$, and X, but are different in number of carbon atoms of each of $R^1$ and $R^2$.

12. The compound according to claim 1, wherein when a compound in which $A^2$ is —O—$CH_2$—CH(—O(-$A^{21}$O)$_m$—H)(—$CH_2$—O(-$A^{22}$O)$_n$—H) is defined as T1, and a compound in which $A^2$ is —O—CH(—$CH_2$—O(-$A^{23}$O)$_s$—H)(—$CH_2$—O(-$A^{24}$O)$_t$—H) is defined as T2, the molar proportion [T1/(T1+T2)] of T1 to the total of T1 and T2 is 0.5 or more and 0.9 or less.

13. The compound according to claim 1, wherein the alkanediyl group is one or more selected from a 1,2-alkanediyl group.

14. The compound according to claim 1, wherein the total of l, m, and n, and the total of l, s, and t are each independently 3 or more and 40 or less.

15. The compound according to claim 1, wherein the total of l, m, and n, and the total of l, s, and t are each independently 5 or more and 30 or less.

16. A method for producing the compound according to claim 1, comprising a process of adding an alkylene oxide having 2 or more and 8 or less carbon atoms to a precursor compound represented by the chemical formula (2) below:

[Chemical Formula (2)]

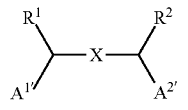

wherein $R^1$ and $R^2$ are each an aliphatic hydrocarbon group, X is a single bond or a hydrocarbon group having 1 or more and 5 or less carbon atoms, a total number of carbon atoms of $R^1$, $R^2$, and X is 2 or more and 39 or less, $A^{1'}$ is —OH, and $A^{2'}$ is —O—$CH_2$—CH(OH)—$CH_2$OH or —O—CH(—$CH_2$OH)$_2$.

17. The method according to claim 16, wherein X is a single bond in the chemical formula (2).

18. The method according to claim 16, wherein the compound represented by the chemical formula (2) comprises two or more compounds that have a same total number of carbon atoms of $R^1$, $R^2$, and X, but are different in number of carbon atoms of each of $R^1$ and $R^2$.

19. The method according to claim 16, wherein the total number of carbon atoms of $R^1$, $R^2$, and X is 10 or more and 20 or less.

20. The method according to claim 16, wherein $R^1$ and $R^2$ are each a linear or branched alkyl group.

* * * * *